(12) United States Patent
Little et al.

(10) Patent No.: US 8,685,039 B2
(45) Date of Patent: Apr. 1, 2014

(54) MEDICAL RETRIEVAL DEVICE WITH FRANGIBLE BASKET

(75) Inventors: William R. Little, Medway, MA (US);
Jason W. Kear, Bloomington, IN (US);
David W. Robertson, Framingham, MA (US); James Teague, Spencer, IN (US);
James W. Riley, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 524 days.

(21) Appl. No.: 12/656,283

(22) Filed: Jan. 22, 2010

(65) Prior Publication Data
US 2011/0028987 A1 Feb. 3, 2011

Related U.S. Application Data

(63) Continuation of application No. 10/342,785, filed on Jan. 15, 2003, now Pat. No. 7,678,119.

(51) Int. Cl.
*A61B 17/22* (2006.01)
*A61B 17/24* (2006.01)

(52) U.S. Cl.
USPC .......................................... 606/127; 606/113

(58) Field of Classification Search
CPC . A61B 17/22; A61B 19/30; A61B 2017/2212
USPC ................. 606/110, 113, 108, 127, 128, 200; 600/11, 12
See application file for complete search history.

(56) References Cited

U.S. PATENT DOCUMENTS 2,054,149 A 9/1936 Wappler
4,493,320 A 1/1985 Treat (Continued)

FOREIGN PATENT DOCUMENTS

WO WO 93/15671 8/1993
WO WO 99/48429 9/1999

(Continued)

OTHER PUBLICATIONS

International Search Report for International Patent Application No. PCT/US02/00383, dated Sep. 12, 2002, 9 pages.

(Continued)

*Primary Examiner* — Julian W Woo
(74) *Attorney, Agent, or Firm* — Bookoff McAndrews, PLLC

(57) ABSTRACT

The invention relates to a medical retrieval device with a basket that has at least one leg that is frangible (i.e., easily breakable) and/or able to dissociate from at least one other leg upon the application of a predetermined force to the basket. The invention allows an operator to release captured material (e.g., a stone) from the basket when the device is still inserted in the body. In an embodiment, the basket legs associate by a magnetic interaction that can be overcome by applying a predetermined force to the basket. In another embodiment, at least a portion of at least one basket leg is made from, or coated with, a substance that is adhesive or that joins at least two legs together when the substance is solid but which melts, dissolves or weakens upon the application of an electrical, thermal or chemical change. In yet another embodiment, the invention provides a basket with at least two legs that are joined together by a joining member that can break, or from which one or more legs can dissociate, upon the application of a predetermined force. In yet another embodiment, the invention provides a basket with at least two legs that are joined together by a joining member by means of at least one shear pin that can break upon the application of a predetermined force.

16 Claims, 13 Drawing Sheets

(56) References Cited

U.S. PATENT DOCUMENTS

| | | | |
|---|---|---|---|
| 4,590,938 | A | 5/1986 | Segura et al. |
| 4,899,744 | A * | 2/1990 | Fujitsuka et al. ............ 606/153 |
| 5,176,688 | A | 1/1993 | Narayan et al. |
| 5,374,273 | A | 12/1994 | Nakao et al. |
| 5,462,553 | A | 10/1995 | Dolgin |
| 5,944,728 | A * | 8/1999 | Bates ........................... 606/127 |
| 6,059,793 | A | 5/2000 | Pagedas |
| 6,083,220 | A | 7/2000 | Guglielmi et al. |
| 6,096,053 | A | 8/2000 | Bates |
| 6,152,932 | A | 11/2000 | Ternstrom |
| 6,159,220 | A | 12/2000 | Gobron et al. |
| 6,187,017 | B1 | 2/2001 | Gregory, Jr. |
| 6,224,612 | B1 | 5/2001 | Bates et al. |
| 6,264,664 | B1 | 7/2001 | Avellanet |
| 6,319,262 | B1 | 11/2001 | Bates et al. |
| 6,673,080 | B2 | 1/2004 | Reynolds et al. |
| 6,971,147 | B2 * | 12/2005 | Halstead ........................ 24/303 |
| 2001/0001315 | A1 | 5/2001 | Bates et al. |
| 2002/0091394 | A1 | 7/2002 | Reynolds et al. |
| 2002/0173817 | A1 | 11/2002 | Kletschka et al. |
| 2003/0233117 | A1 | 12/2003 | Adams et al. |

FOREIGN PATENT DOCUMENTS

| | | |
|---|---|---|
| WO | WO 00/71036 A2 | 11/2000 |
| WO | WO 01/10290 A2 | 2/2001 |
| WO | PCT/US01/13065 | 4/2001 |

OTHER PUBLICATIONS

PCT International Search Report for International Application No. PCT/US2004/001009, dated Jul. 19, 2004.

* cited by examiner

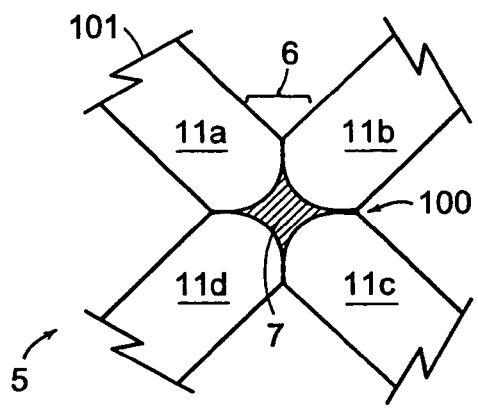
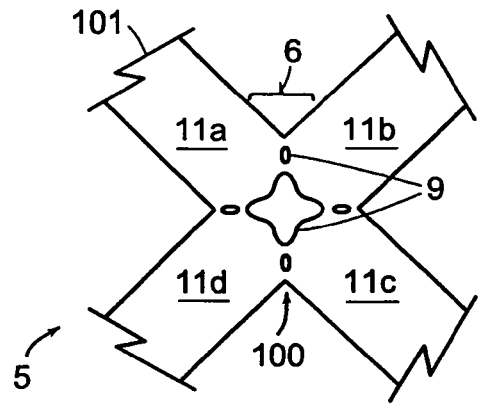
FIG. 3A
FIG. 3B
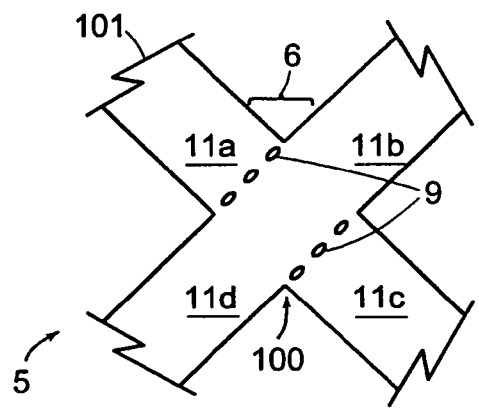
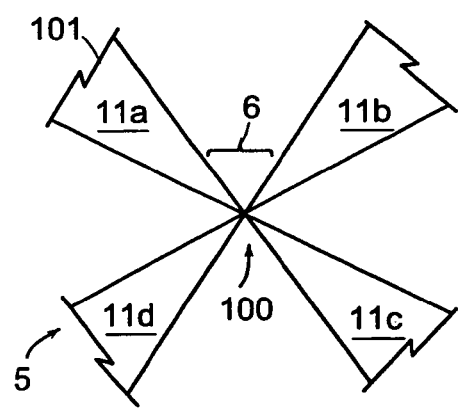
FIG. 3C
FIG. 3E

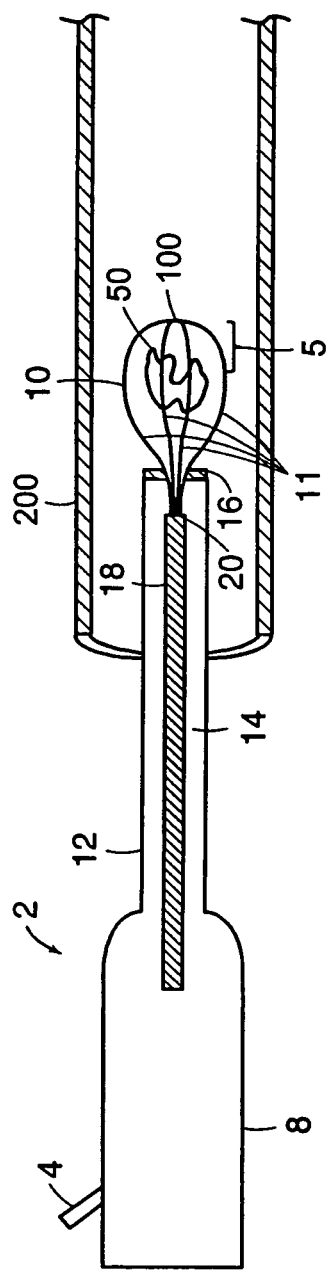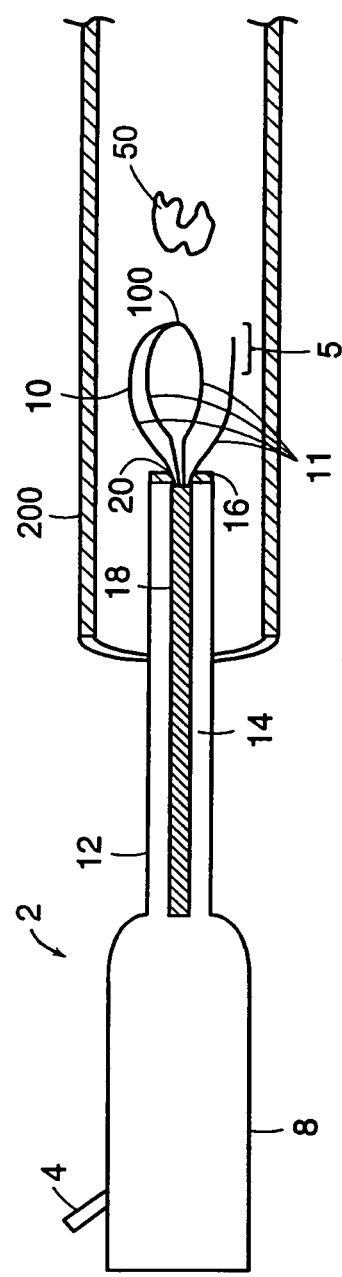

MEDICAL RETRIEVAL DEVICE WITH FRANGIBLE BASKET

This is a continuation of application Ser. No. 10/342,785, filed Jan. 15, 2003, now U.S. Pat. No. 7,678,119, which is incorporated herein by reference.

TECHNICAL FIELD

The invention relates generally to medical retrieval devices for retrieving material from within a body. More particularly, the invention relates to a medical retrieval device with a basket that has at least one leg that is breakable and/or dissociates from the end of the basket upon the application of a predetermined force, to allow release of captured material (e.g., a stone).

BACKGROUND OF THE INVENTION

Typical medical retrieval devices have baskets that are constructed by joining multiple legs together at the proximal end of the basket (i.e., the end of the basket closest to the operator) and at a distal end of the basket (i.e., the end of the basket furthest to the operator) such that a "cage" is formed. At the distal end of the basket, the individual legs are typically joined by soldering, adhesives, etc., such that material (e.g., a stone) can be captured in the basket and remain captured until the basket is removed from the body. A typical basket is introduced into a body tract via an endoscope or catheter and maneuvered around the material until the material enters the basket. If it is necessary to reduce the size of the material, the material is then fragmented, typically by applying tension to the basket wires surrounding the material until sufficient force is applied directly to the material by the basket wires to cause the material to break apart.

Under certain circumstances, however, it is desirable to release the material from the basket before removal of the retrieval device from the body. For example, a stone may become trapped within the basket of the retrieval device (e.g., due to the large size of the stone) and attempts to remove the retrieval device with the stone may traumatize the lining of the body tract. In addition, failure of the medical retrieval device or its components may occur. For example, failure of the actuating mechanism that operates the movement of the basket relative to the sheath of the device may impede the ability of the device to crush the stone, or the basket wires may become dissociated from the guide wire to which they are attached. In those circumstances, the inability to remove the device from the patient may require additional, more invasive, and potentially life-threatening surgical procedures in order to disengage the stone from the basket and to remove the basket from the body tract.

SUMMARY OF THE INVENTION

It is an object of the invention to provide medical retrieval devices with a basket that has at least one leg that is capable of breaking and/or is capable of dissociating from the other legs of the basket. In an embodiment, the at least one basket leg is frangible (i.e., easily breakable) or has a frangible portion, e.g., at its distal end portion. In another embodiment, the basket legs associate by a magnetic interaction. The magnetic association can be overcome by applying a predetermined force to the basket or at least one basket leg. In another embodiment, at least a portion of at least one basket leg includes a substance that keeps the leg together and/or joins it to the other legs. The substance melts, dissolves or weakens in response to applying, or exposure to, an electrical, thermal or chemical change to the substance, causing at least one basket leg to break or to dissociate from at least one other basket leg. In yet another embodiment, the invention provides a basket with legs that are joined together by a joining member by means of shear pins that can break upon the application of a predetermined force to the basket legs. In another embodiment, the shear pin comprises a substance that is sticky or gluey, or is altered by an electrical, chemical, magnetic, or thermal change. In another embodiment, the joining member is a tube through which the basket legs pass and within the lumen of which the legs are joined to each other and/or to the joining member. At least one basket leg according to the invention is capable of breaking or dissociating from the other legs in response to an applied force in order to release captured material prior to removal of the device from the body.

It is yet another object of the invention to provide methods of using such baskets to retrieve material from within a body, as well as methods that provide for the release of material from the basket while the basket is in the body. Retrieval baskets and methods of the invention may be used to retrieve one or more materials, e.g., calculi, stones, and/or other objects from a body tract such as a biliary or pancreatic duct, hepatic duct, cystic duct, common bile duct, ureter, urinary bladder, urethra, or kidney.

In one aspect, the invention relates generally to a sheath with a proximal end, a distal end, a handle at the proximal end of the sheath, and a basket with a plurality of legs having a collapsed position when the basket is within the sheath and collapsed and an expanded position when the basket is positioned beyond the distal end of the sheath and expanded. In one embodiment, at least one of the legs has a frangible portion such that the at least one leg is capable of breaking and/or dissociating from the other legs upon the application of a predetermined force to the basket. The break point may be made by altering the structural integrity of at least a portion of at least one leg by laser etching, laser cutting, stamping, or by inclusion of at least one perforation or one notch, for example.

In another embodiment, the invention provides a medical retrieval device with a basket having a plurality of legs, at least one of which has a magnetic portion. The magnetic portion attracts, or is attracted to, at least one other leg, preferably all of the other legs, thereby allowing them to associate with one another. Upon the application of a predetermined force to the basket legs, the legs dissociate, allowing material that may be captured in the basket to be released. In one embodiment, the magnetic portion of the one or more legs is capable of re-associating (i.e., rejoining the other leg(s)) after dissociating. In another embodiment, the magnetic portion comprises a magnetic member joined to at least one basket leg, which is attracted magnetically to at least one other member. The magnetic member may provide a greater magnetic surface area and therefore a greater magnetic attraction between legs than the distal end portion of the legs without the magnetic member. The magnetic member may be associated with more than one leg and may associate with at least one other member. The magnetic members that are associated may dissociate upon the application of a predetermined force and are capable of re-associating after dissociating.

In another embodiment, at least a portion of at least one leg is manufactured from a substance that is altered by an electrical current (i.e., an electrically alterable substance). Preferably, the electrical current has an energy that does not damage tissue. In an embodiment, the electrically alterable substance joins together at least two of the basket legs at their distal end portion. Upon the application of an electrical current, the physical characteristics of the electrically alterable substance are altered such that the electrically alterable substance melts, dissolves or softens, thereby weakening the at least one leg or the association of the at least two legs. The weakened leg then breaks or the at least two legs then dissociate and material captured within the basket is released. The electrically alterable substance that is altered by an electrical current may be a metal, such as e.g., stainless steel, platinum, or gold, or a conductive polymer, such as e.g., polyacetylene, polyaniline or polyphenylene. One or more of the legs may be coated at least partially with a resistive or insulative covering, such as that described in U.S. Pat. No. 6,425,914, the entire disclosure of which is incorporated by reference.

In another embodiment, at least a portion of at least one leg is manufactured from a substance that is altered by a thermal change (i.e., a thermally alterable substance). Preferably, the thermal change is to a temperature that is lower than a temperature that damages tissue. In an embodiment, the thermally alterable substance joins together at least two of the legs at their distal end portion. Upon the application of a thermal change, the physical characteristics of the substance are altered such that the thermally alterable substance melts, dissolves or softens, thereby weakening the at least one leg or the association of the at least two legs. The weakened leg then breaks or the at least two legs then dissociate and material captured within the basket is released. Exemplary thermally alterable substances that are altered by a thermal change include ethylene-vinyl acetate and ethylene-methyl acrylate.

In another embodiment, at least a portion of at least one leg is manufactured from a substance that is altered by a chemical change (i.e., a chemically alterable substance). Preferably, the chemical change does not damage tissue. In an embodiment, the chemically alterable substance joins together at least two of the legs at their distal end portion. Upon applying a chemical change, the physical characteristics of the chemically alterable substance are altered such that the substance melts, dissolves or softens, thereby weakening the at least one leg or the association of the at least two legs. The chemical change may be caused by exposure to an enzyme or other chemical known in the art that alters the physical characteristics of the chemically alterable substance. The weakened leg then breaks or the at least two legs dissociate and the material captured within the basket is released. The chemically alterable substance that is altered by an enzymatic, ionic, or pH chemical change may be, for example, hydroxapetite, acrylic-methacrylic acid, or ethylcellulose.

In another embodiment, at least a portion of at least one leg is manufactured from an adhesive substance. Preferably, the adhesive substance does not adhere to or otherwise damage tissue. In an embodiment, the adhesive substance joins together at least two of the legs at their distal end portion. Upon applying a predetermined force to the basket, the at least one leg breaks or the at least two legs dissociate and material captured within the basket is released. The adhesive substance may be, for example, acrylic-methacrylic acid, silicone, urethane, or isoctylacrylate.

In another embodiment, the invention provides a medical retrieval device that has a sheath with a proximal end and a distal end, a handle at the proximal end of the sheath and a basket having a collapsed position when the basket is positioned within the sheath and collapsed and an expanded position when the basket is positioned beyond the distal end of the sheath and expanded, wherein the basket has a plurality of legs that are joined at their distal end portions by a joining member. The joining member is joined to the legs by at least one shear pin. The legs are capable of dissociating upon the application of a predetermined force to the at least one shear pin. In one embodiment, the shear pin has a waist. In another embodiment, at least a portion of the shear pin is made of an adhesive substance or a substance that is altered by an electrical, chemical, thermal, or magnetic change. In another embodiment, the joining member is a tube through which the legs of the basket may pass, wherein at least the distal end portion of the legs are joined either to each other or to the joining member within the lumen of the tubular joining member.

In another aspect, the invention provides methods for removing material from a body tract using a medical retrieval device having a sheath with a proximal end and a distal end, a handle at the proximal end of the sheath and a basket having a collapsed position when the basket is positioned within the sheath and collapsed and an expanded position when the basket is positioned beyond the distal end of the sheath and expanded. The basket includes a plurality of legs of which at least one has a frangible portion comprising a break point. The device is inserted into a body tract, the basket is moved into an extended position, and the device is maneuvered until the material in the body tract is captured inside the basket. The basket is then moved into a retracted position and the device is withdrawn from the body tract. Alternatively, a predetermined force is applied to the basket while the basket is still inserted into the body tract, causing the at least one leg to break or to dissociate from the other legs, and releasing the captured material from the basket.

In another aspect, the invention provides methods for removing material from a body tract using a medical retrieval device having a sheath having a proximal end and a distal end, a handle at the proximal end of the sheath and a basket having a collapsed position when the basket is positioned within the sheath and collapsed and an expanded position when the basket is positioned beyond the distal end of the sheath and expanded. The basket has a plurality of legs of which at least one has a magnetic portion. The device is inserted into a body tract, the basket is moved into an extended position, and the device is maneuvered until the material is captured inside the basket. The basket is then moved into a retracted position and the device is withdrawn from the body tract. Alternatively, a predetermined force is applied to the basket while the basket is still inserted into the body tract, causing the magnetic portion of one leg to dissociate from another leg, releasing the captured material from the basket. In another embodiment, the magnetic portion(s) of at least one or more legs can re-associate after dissociation.

In another aspect, the invention provides methods for removing a material from a body tract using a medical retrieval device having a sheath having a proximal end and a distal end, a handle at the proximal end of the sheath and a basket having a collapsed position when the basket is positioned within the sheath and collapsed and an expanded position when the basket is positioned beyond the distal end of the sheath and expanded. The basket includes a plurality of legs in which at least two legs are joined to a joining member by at least one shear pin. The at least one shear pin breaks upon the application of a predetermined force, allowing the at least two legs to dissociate. The device is inserted into a body tract, the basket is moved into an extended position, and the device is maneuvered until the material is captured inside the basket. The basket is then moved into a retracted position and the device is withdrawn from the body tract. In an embodiment, a predetermined force is applied to the basket, causing the at least one shear pin to break and the at least two legs to dissociate, releasing the captured material from the basket. In an embodiment, the joining member is a tube through which the legs of the basket may pass, the distal end portion of the legs joined to each other or to the joining member within the lumen of the tubular joining member. In one embodiment, the tubular member is cross-shaped. In an embodiment, a predetermined force is applied to the basket, causing at least one leg to dissociate from the other legs within the joining member or from the joining member, and causing the release of the captured material from the basket.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 3A illustrates an end view of one embodiment of a basket with legs having a distal end portion having a weakness or break point.

FIG. 3B illustrates an end view of another embodiment of a basket according to the invention with legs having a distal end portion having a break point.

FIG. 3C illustrates an end view of another embodiment of a basket according to the invention with a distal end portion having a break point.

FIG. 3E illustrates an end view of one embodiment of a basket according to the invention with a distal end portion having a break point containing tapered basket leg tips.

FIG. 8D illustrates one embodiment of a medical retrieval device with a basket according to the invention with the basket in an expanded position containing a captured material.

FIG. 8E illustrates one embodiment of a medical retrieval device with a basket according to the invention with a broken basket in an expanded position and a released material.

DETAILED DESCRIPTION OF THE INVENTION

All of the following embodiments of the medical devices according to the invention generally have at least one thing in common, a basket having a plurality of legs of which at least one leg is capable of breaking or dissociating from the other legs upon application of a predetermined force to the basket.

Figure 1A:
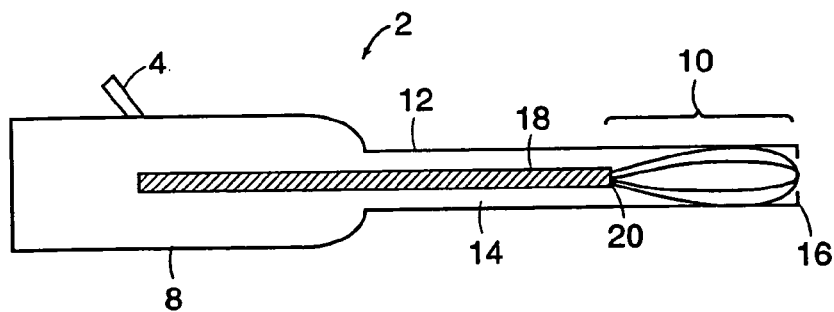
FIG. 1A illustrates one embodiment of a medical retrieval device with a basket according to the invention with the basket in a collapsed position.
Figure 1B:
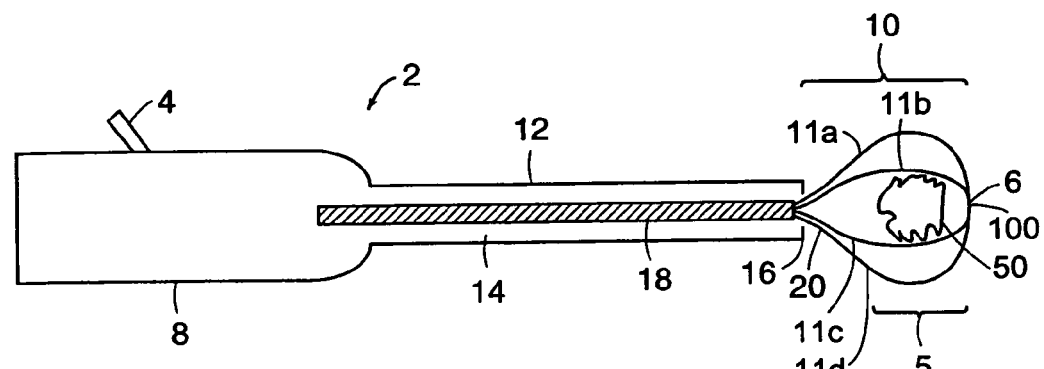
FIG. 1B illustrates one embodiment of a medical retrieval device with a basket according to the invention with the basket in an expanded position.
Figure 1C:
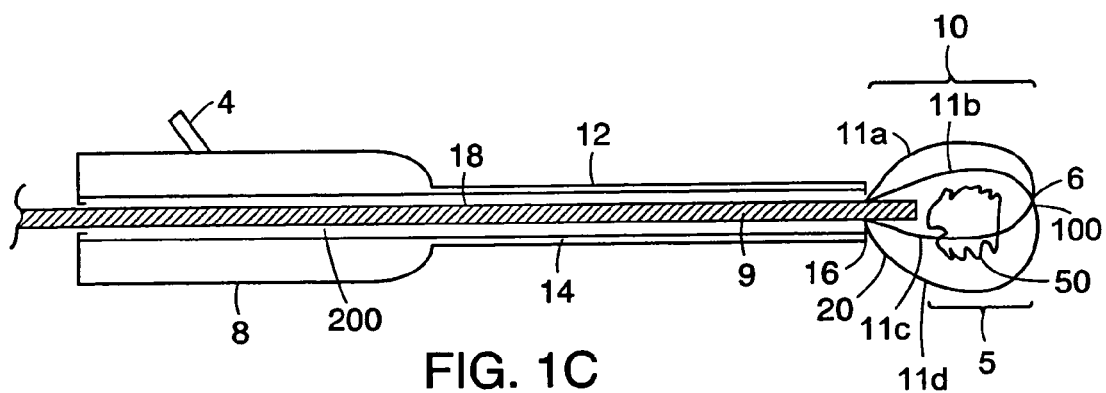
FIG. 1C illustrates an embodiment of the medical retrieval device according to the invention with a lithotripsy device extending into the basket lumen.

Referring to FIGS. 1A and 1B, a medical retrieval device 2 includes a basket 10, a sheath 12 and a proximal handle 8. The handle 8, sheath 12, and basket 10 illustrated in FIGS. 1A, 1B, and 1C are not shown in their correct size or proportion to each other. The size of the entire sheath 12 is dimensioned to fit the requirements of its application in the body. For example, for urological applications, the size of the sheath 12 is typically 1.7-8.0 French. The sheath 12 has at least one lumen 14 therein and extends from the handle 8 to a distal sheath end 16. In one embodiment according to the invention, an elongated member 18 such as a cable, coil, shaft, guide wire, or mandril wire extends within the sheath lumen 14 from an actuating mechanism 4 on the device handle 8 and is attached to the proximal end of the basket 20. Operation of the actuating mechanism 4 on the handle 8 by an operator causes the basket 10 to move in and out of the sheath 12 between a collapsed position within the lumen 14 of the sheath 12, as illustrated in FIG. 1A, to an extended position outside of the sheath 12, where the basket 10 is open/expanded and extending beyond the distal sheath end 16, as shown in FIG. 1B. Alternatively, the mechanism 4 can cause movement of the sheath 12 to advance the sheath 12 over a stationary basket 10 and elongated member 18 combination, to thereby collapse the basket 10 within the lumen 14 of the sheath 12, and the mechanism 4 can slide the sheath 12 back to expose the stationary basket 10 and allow the basket 10 to open/expand again.

With the basket 10 collapsed within the sheath 12, as shown in FIG. 1A, the sheath 12 can be inserted by an operator into a site in the body (e.g., a body tract, lumen or cavity) where material 50, for example, a biliary stone, to be retrieved is located. By placing the basket 10 into its open/expanded position, as illustrated in FIG. 1B, the basket 10 may dilate the body tract in which the basket 10 has been placed and can be manipulated by the operator to enclose material 50 within the basket 10. The basket 10 and/or the sheath 12 can then be moved to cause the basket 10 to close around the material 50 and capture the material 50. Under normal circumstances, the captured material 50 is then removed from the body along with the sheath 12 and the basket 10.

In some clinical situations it is desirable to fragment the captured material 50. Referring to FIG. 1C, for example, when the combination of the material 50 and basket 10 is too large to be withdrawn atraumatically from the body tract, the material 50 may be fragmented by, for example, a mechanical lithotripsy device 9. In another embodiment, the material 50 may be fragmented by applying tension to the basket 10.

Figure 2A:
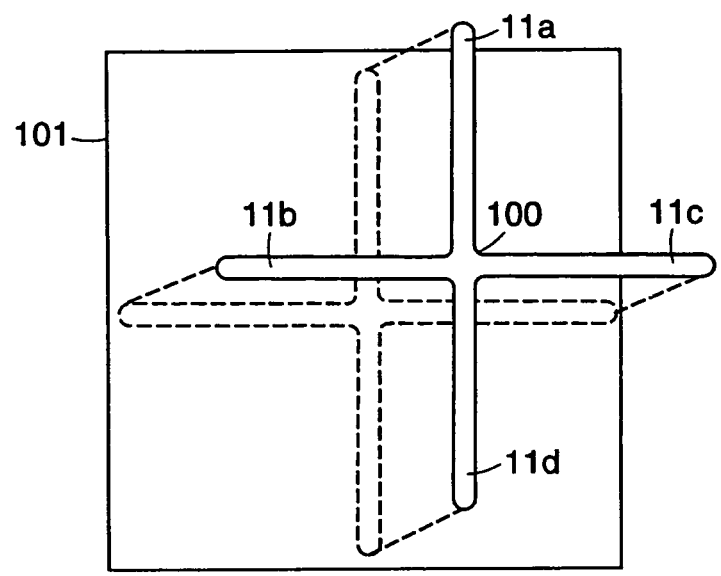
FIG. 2A illustrates a top view of an X-shape embodiment of a one-piece unit of at least a distal end portion of the legs that is removed from a single piece of substantially flat material according to the invention.
Figure 2B:
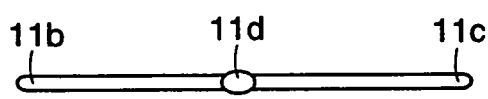
FIG. 2B illustrates a side view of the one-piece unit illustrated in FIG. 2A.
Figure 2C:
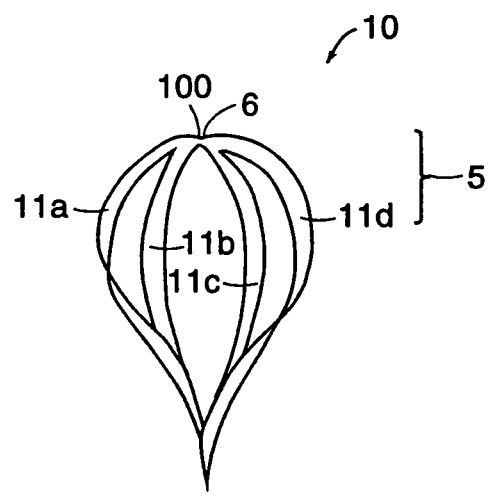
FIG. 2C illustrates a side view of an embodiment according to the invention of a three-dimensional basket formed by bending and shaping the legs of the one-piece unit illustrated in FIG. 2A.
Figure 2D:
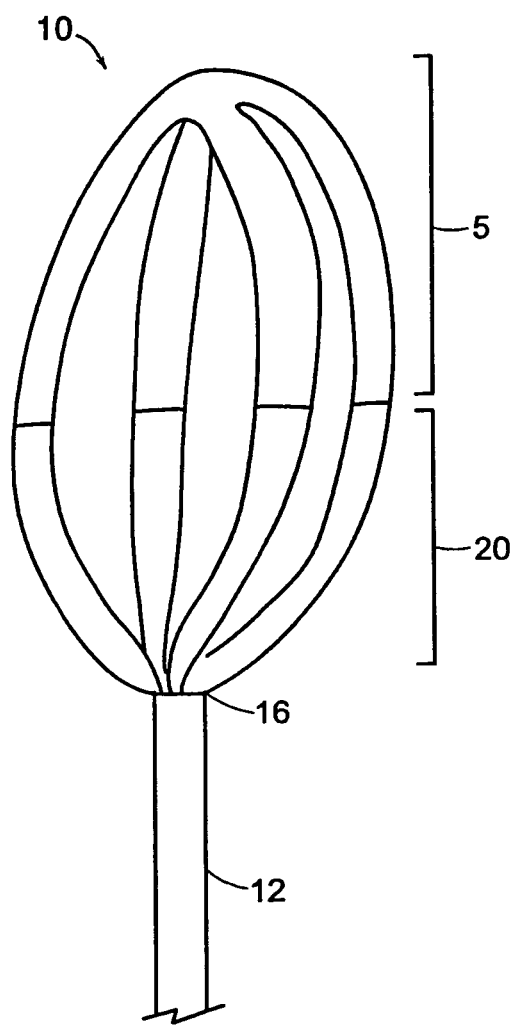
FIG. 2D illustrates a side view of an embodiment according to the invention of a three-dimensional basket formed by bending and shaping the distal end portion of basket legs removed from a single piece of substantially flat material and joining them to the proximal end of the basket legs.

Referring to FIG. 1B, in one embodiment the basket 10 includes a plurality of legs 11 (e.g., 11a, 11b, 11c, and 11d) that each have a distal end portion 5. The legs 11 join or associate at the distal tip 100 of the legs 11. In one embodiment, the legs 11a, 11b, 11c, and 11d or a portion of the legs 11a, 11b, 11c, and 11d may be cut, etched, stamped or otherwise removed as a single defined shape from a substantially flat piece of construction material 101, as viewed from the top in FIG. 2A and the side in. FIG. 2B. FIG. 2C, for example, illustrates a single integral unit such as the shape illustrated in FIG. 2A, which is folded to make a basket 10 according to the invention. In another embodiment, illustrated in FIG. 2D, the distal end portion 5 of the legs 11 of the basket 10, which is removed as a single defined shape from a substantially flat piece of construction material 101, is attached to the proximal end portion 20 of the basket 10, e.g., by gluing, soldering or welding. In another embodiment, the legs 11 or distal end portion 5 of the legs 11 can be injection molded into the desired shape by, for example, plastic injection molding, metal-injection-molding (MIM) or by compression of metal powders. The basket 10 may be formed by assembling a plurality of individual legs 11 and joining together the distal end portion 5 of the legs 11. Typically, the length of the legs 11 is about 0.5 to about 3.5 inches, for example, about 1.1 to about 1.5 inches, the width of the legs 11 is about 0.005 inches to about 0.015 inches and the thickness of the legs 11 is about 0.028 inches to about 0.045 inches.

Figure 3D:
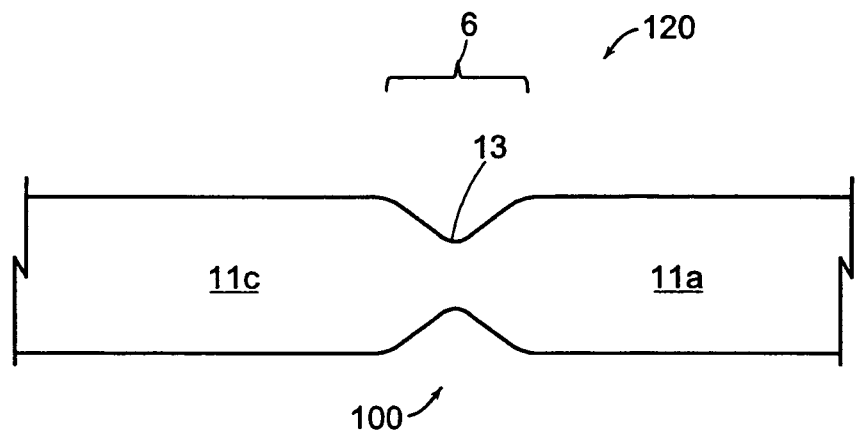
FIG. 3D illustrates a side view of one embodiment of a basket according to the invention with a distal end portion having notches.

With reference to FIGS. 3A-3E, according to the invention, at least one of the legs 11 includes a frangible portion comprising a break point 6. In an embodiment, the frangible portion or break point 6 is positioned in a region in the distal end portion 5 of a leg 11 that is weaker, i.e., more susceptible to breaking, than the other portions of the leg 11. When a predetermined force, e.g., a force that is more than the force required for capturing and holding material 50, is applied to the basket 10 or is applied to at least one leg 11, the leg 11 breaks at break point 6 causing the basket 10 to fail. When the basket 10 fails, material 50 captured in the basket 10 can escape from the basket 10. The break point 6 can be positioned at any point along at least one or more legs. In an embodiment, the break point 6 is positioned at the distal tip 100 of the legs 11. The distal tip 100 of the legs 11 may be positioned on a distal end portion 5 of at least one leg 11, that is formed from a single sheet of material and joined to the basket legs, as illustrated in FIGS. 2A-2C. Alternatively, the distal tip 100 may be the point at which the legs 11 are joined at the distal end portion 5 of the legs 11. Referring to FIG. 3A, for example, the break point 6 may be a portion 7 of at least one leg 11 of the basket 10, which is thinner and more readily breakable than the remainder of the at least one leg 11. The thin portion 7 is frangible relative to the remainder of the at least one leg 11 and is breakable upon application of a predetermined force to the basket 10. In one embodiment, the thickness of the thin portion 7 of the leg 11 at the break point 6 is between about 0.001 and about 0.015 inches or about 10%-85% thinner than the remainder of the leg.

In another embodiment according to the invention, referring now to FIGS. 3B and 3C, for example, the break point 6 may have one or more perforations 9 at any point along at least one leg 11. In an embodiment, the perforations are present in the distal end portion 5 of the leg 11. The perforations 9 may extend partly through, or completely through, the thickness of the at least one leg 11. The perforations may be arranged in a star pattern, for example, as illustrated in FIG. 3B, a linear pattern as illustrated in FIG. 3C, or arranged in any pattern that provides a point of structural weakness to at least one leg 11, causing the at least one leg 11 to break when a predetermined force is applied to the basket 10 (e.g., to at least one leg 11).

In another embodiment according to the invention, referring now to FIG. 3D, for example, the break point 6 may include at least one notch 13 where two legs 11 are joined. In an embodiment, the notch 13 is positioned at the distal end portion 5 of the legs 11. In an embodiment, the distal end portion 5 of at least two legs 11a and 11c is tapered such that where the distal end portion 5 of the legs 11a, 11c are joined, a notch 13 is formed. The notch 13 weakens the distal portion 5 of the legs 11a and 11c, thereby creating a break point 6 between the legs 11a and 11c. In an embodiment, the notch 13 is positioned at the distal tip 100 of at least two legs 11.

The thin portion 7, perforations 9, or notch 13, for example, may be introduced into at least one leg 11 by laser etching, laser cutting, or stamping. In a preferred embodiment, the break point 6 is located at the distal tip 100 of one or more legs 11, but may also be on any portion of the legs 11, for example, the distal end portion 5 of at least one leg 11.

In one embodiment according to the invention, for example, illustrated in FIG. 3E, at least one leg 11a, 11b, 11c and 11d is tapered. In a preferred embodiment, the legs 11a, 11b, 11c, 11d are all tapered. The taper may begin anywhere along the long axis of the at least one leg 11. The taper may begin, for example, at the mid-point of the length of the at least one leg 11 or may begin in the distal end portion 5 of the at least one legs 11. In an embodiment, the taper proceeds toward the distal end portion 5 of the at least one leg 11. Where the tapered legs 11 are joined is the break point 6 of the basket 10.

The various embodiments of the break point 6 or the distal end portions 5 on the at least one leg 11 are not limited to those illustrated in the Figures but may include other shapes and configurations not illustrated that weaken at least one leg 11.

The legs 11, and the distal end portion 5 of the legs 11, can be formed from various materials such as sterling silver, stainless steel, NiTi (e.g., nitinol), metal alloys, superelastic materials, shape memory materials, powdered metals, ceramics, thermal plastic composites, ceramic composites, other composites, and/or polymers. In one embodiment, the proximal end portion 20 of the legs 11, and the distal end portion 5 of the legs 11 may be manufactured from different materials and joined together as described previously.

Figure 4:
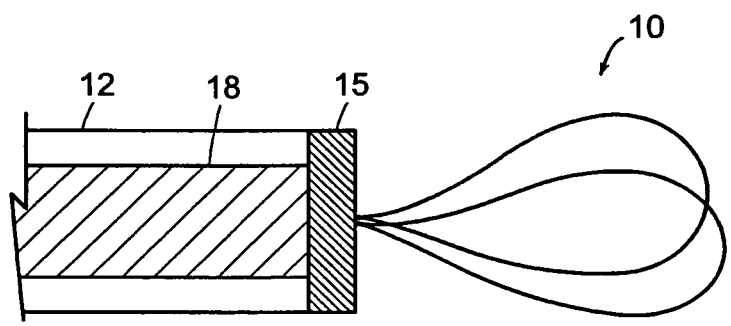
FIG. 4 illustrates an embodiment of a sheath of the invention having a metal ring at its distal end.

The sheath 12 of the medical retrieval device 2 is manufactured from (e.g., polyimide, PTFE, composites or similar construction materials. Referring to FIG. 4, in one embodiment according to the invention a metal ring 15 is inserted into the lumen 14 of the sheath distal end 16 to resist splitting of the sheath distal end 16. The metal ring 15 may be flush with the distal end 16 of the sheath 12 or, alternatively, may protrude slightly beyond the distal end 16 of the sheath 12.

Figure 5A:
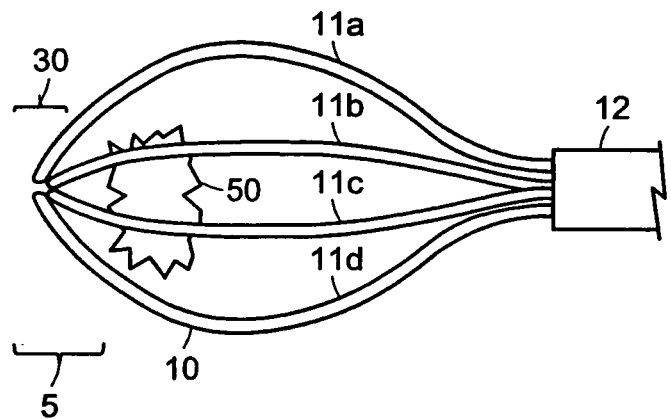
FIG. 5A illustrates an embodiment of a basket according to the invention in which the distal end portions of the basket legs are joined by a magnetic interaction.

Referring to FIG. 5A, in another embodiment according to the invention at least a portion of at least one leg 11a, 11b, 11c, 11d, for example, leg 11a, may have a magnetic portion 30 that attracts, or is attracted to, at least one other leg 11, for example, leg 11d, such that the magnetic attraction allows the leg 11a with the magnetic portion 30 to be reversibly joined magnetically to the leg 11d. The magnetic portion 30 of at least a portion of at least one leg 11a creates a magnetic field that attracts another leg 11. The other leg 11, for example, leg 11d as shown in FIG. 5a, may be made from certain metals (such as, e.g., iron, cobalt, nickel, gadolinium, and/or dysprosium), an alloy containing one or more of those metals, a paramagnetic material (such as, e.g., aluminum), and/or a magnetic alloy (such as, e.g., permalloy, supermalloy, and/or μ-metal).

Figure 5B:
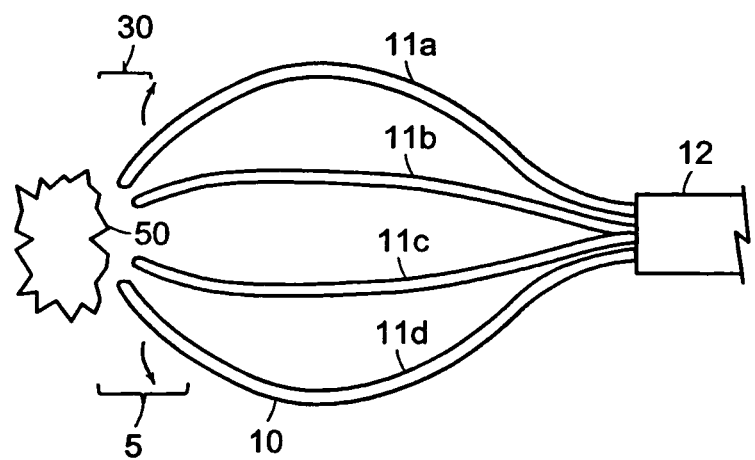
FIG. 5B illustrates the basket illustrated in FIG. 5A in which the distal end portions of the basket legs are released.

Referring to FIG. 5B, the magnetic portion 30 of at least one leg 11a, 11b, 11c, 11d, for example leg 11a, dissociates from the other non-magnetic legs 11, for example, leg 11b, 11c, 11d upon the application of a predetermined force to the basket 10 or to at least one leg 11, and/or upon a change in magnitude of magnetic energy generated at the magnetic portion 30. In one embodiment according to the invention, the legs 11a, 11b, 11c, 11d are pre-stressed such that the legs 11a, 11, 11c, 11d, e.g., the distal end portion 5, move away from each other when the magnitude of the magnetic field is diminished.

Figure 5C:
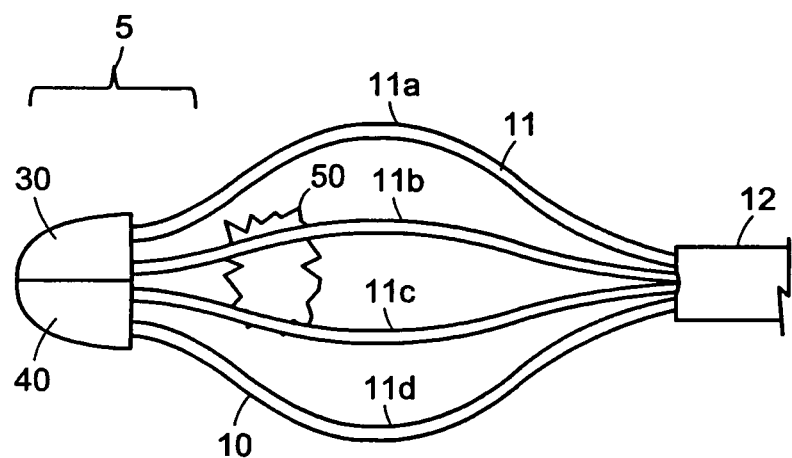
FIG. 5C illustrates an embodiment of a basket according to the invention in which the distal end portions of the legs have magnetic members.
Figure 5D:
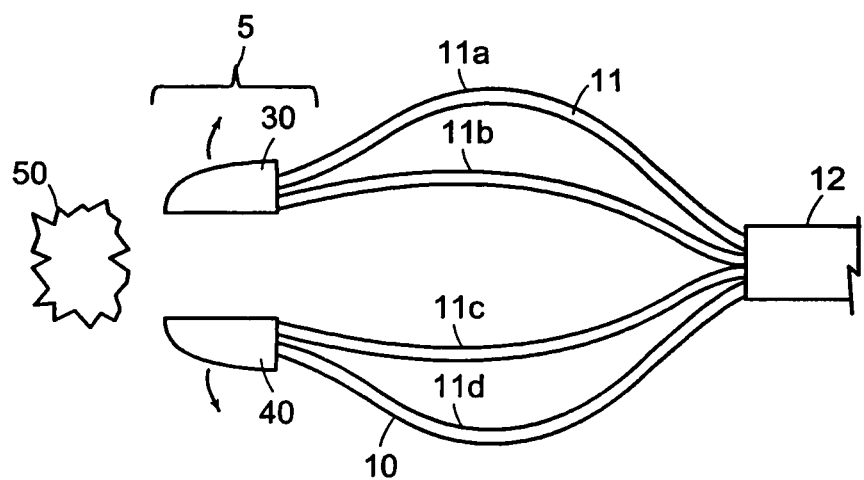
FIG. 5D illustrates the basket illustrate in FIG. 5C in which the distal end portion of the basket legs are released.

In one embodiment, illustrated in FIG. 5C, a basket 10 comprises legs 11a, 11b, 11c, 11d. At least one leg 11a, 11b, 11c, 11d includes a magnetic first member 30 and at least one other leg 11a, 11b, 11c, 11d includes a second member 40. In an embodiment, the first member 30 and second member 40 are positioned in the distal end portions 5 of one or more legs 11. For example, the first member 30 is positioned in the distal end portion 5 of the legs 11a, 11b and the second member 40 is positioned in the distal end portion 5 of the legs 11c, 11d, as illustrated in FIGS. 5C and 5D. The magnetic first member 30 and second member 40 are magnetically attracted to one another such that the magnetic first member 30 and second member 40 remain reversibly joined magnetically in the presence of a magnetic field generated by at least the first member 30 or the second member 40. The magnetic first member 30 and second member 40 may provide a greater surface area for the interaction of the magnetic first member 30 and the second member 40 than the distal end portions 5 of the legs 11.

Referring to FIG. 5D, upon the application of a predetermined force or a reduction in the magnitude of the magnetic field generated by the magnetic first member 30, the magnetic first member 30 and second member 40 dissociate, i.e., move apart, allowing material 50 captured in the basket 10 to be released from the basket 10 (e.g., into the body cavity). A predetermined force may be applied by, e.g., forcibly retracting the basket toward the sheath 12, thereby forcing the trapped material 50 against the magnetic first member 30 and second member 40, urging the magnetic first member 30 and second member 40 apart, i.e., to dissociate. The predetermined force for urging the magnetic member 30 and the second member 40 apart is greater than the force that keeps the magnetic first member 30 and the second member 40 together. Alternatively, the magnitude of the magnetic field generated by the magnetic first member 30 may be reduced, thereby removing the attraction of the magnetic first member 30 with the second member 40. Preferably, the distal end portions 5 of at least one leg 11 spring apart upon application of a predetermined force or upon the reduction in the magnitude of the magnetic field.

In another embodiment according to the invention, at least one leg 11 of the basket 10 breaks and/or dissociates from at least one other leg 11 of the basket 10 when an electrical potential difference is applied to the at least one leg 11. In an embodiment, the force is applied to the distal end portion 5 of at least one leg 11. At least a portion (e.g., the distal end portion 5) of at least one leg 11 may be manufactured with, or joined to another leg 11 by, a substance (e.g., an electrically alterable substance) with physical characteristics that are altered by a change in electrical potential difference. In an embodiment, a change in the electrical potential difference may cause the physical characteristics of the distal end portion 5 of at least one leg 11 to change, e.g., soften, melt, dissolve or liquefy. The electrical potential is less than the electrical potential that would cause damage to tissue but great enough to alter the physical characteristics of the distal end portion 5 of at least one leg 11. For example, a change in the potential difference may cause a phase change in the physical characteristics of the electrically alterable substance. The electrically alterable substance may be in a first phase, such as a solid, prior to the change in electrical potential difference and transitions to a second softened phase after the change in potential difference, allowing the at least one leg 11 to break and/or to dissociate from the other legs 11. Suitable electrically alterable substances that are useful for the manufacture of at least a part of at least one leg 11 include, but are not limited to, conductive polymers such as e.g., polyacetylene, polyaniline, and polyphenylene and metals, such as, e.g., stainless steel, platinum, and gold.

In another embodiment according to the invention, at least one leg 11 of the basket 10 breaks and/or dissociates from at least one other leg 11 of the basket 10 by imposing a temperature change at the at least one leg 11. In an embodiment, the force is applied to the distal end portion 5 of at least one leg 11. At least a portion (e.g., the distal end portion 5) of at least one leg 11 may be manufactured with, or joined to another leg by a substance (e.g., a thermally alterable substance) with physical characteristics that are altered by a change in temperature. In an embodiment, a change in temperature may cause the physical characteristics of the distal end portion 5 of at least one leg 11 to change, e.g., soften, melt, dissolve or liquefy. The temperature change may be caused by, for example, a low voltage current or a change in the temperature of the irrigation fluid used around the distal end portion 5 of the legs 11. The thermally alterable substance may be in a first phase such as a solid prior to the temperature change and transitions to a second solid phase after the temperature change, allowing the at least one leg 11 to break and/or to dissociate. The temperatures applied to cause a transition from a first to a second phase are not temperatures that cause tissue damage. Suitable thermally alterable substances that are susceptible to temperature change and useful for the manufacture of at least a part of at least one leg 11 include, but are not limited to, ethylene-vinyl acetate and ethylene-methyl acrylate.

In another embodiment according to the invention, at least a portion of (e.g., the distal end portion 5) at least one leg 11 may be manufactured with, or joined to at least one other leg by, a chemically alterable substance. The chemically alterable substance has physical characteristics that are altered by exposure to a substance that causes a change in pH or tonicity, or other change (e.g., enzymatic) that may cause the physical characteristics of the distal end portion 5 of at least one leg 11 to change, e.g., soften, melt, dissolve or liquefy. The chemically alterable substance may be in a first phase such as a solid prior to the chemical change which transitions to a second softened phase after the chemical change, allowing the at least one leg 11 to break and/or dissociate from the other legs 11. The chemical change does not damage tissue. Suitable chemically alterable substances that are susceptible to chemical change and useful for the manufacture of at least a part of at least one leg 11 include, but are not limited to, hydroxyapatite, acrylic-methacrylic acid, and ethylcellulose.

In another embodiment according to the invention, at least one leg 11 of the basket 10 breaks or dissociates from at least one other leg 11 of the basket 10 when a predetermined force is applied to the basket 10. At least a portion of at least one leg 11 may be manufactured from, or coated with, an adhesive substance. Upon applying a predetermined force to the basket 10, the at least one leg 11 breaks. In another embodiment, the adhesive substance joins together at least two of the legs 11, e.g., at their distal end portion 5. Upon applying a predetermined force to the basket 10, the at least two legs dissociate and material captured within the basket 10 is released. Suitable adhesive substances useful for the manufacture of at least a part of at least one leg 11 or used to join the distal end portions 5 of two or more legs 11, include, but are not limited to, acrylic-methacrylic acid, silicone, urethane, and isooctylacrylate.

Figure 6A:
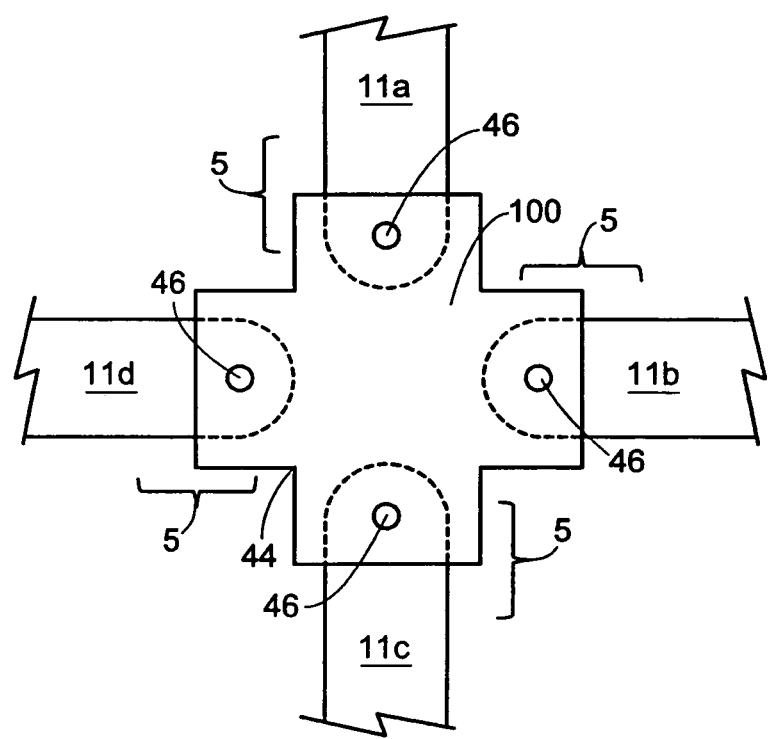
FIG. 6A illustrates an embodiment of the distal end portions of the basket legs according to the invention in which the tips of the basket legs are joined to a joining member by notched shear pins.
Figure 6B:
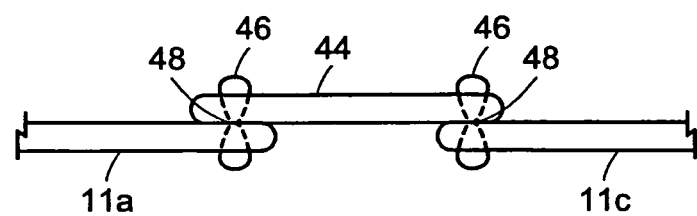
FIG. 6B illustrates a cross-section of the embodiment according to the invention in FIG. 6A in which the tips of the basket legs are joined to a joining member by notched shear pins.
Figure 6C:
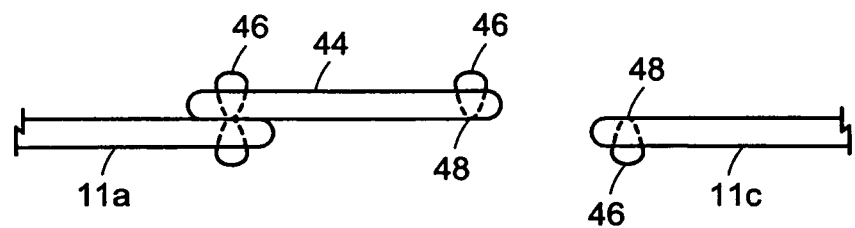
FIG. 6C illustrates a cross-section of the embodiment according to the invention in FIG. 6B in which one of the shear pins has broken and the tip of a basket leg is broken away from the joining member.

In another embodiment according to the invention, illustrated in FIG. 6A, the distal end portion 5 of at least two legs 11 are joined to a joining member 44 by means of at least one shear pin 46. As illustrated in cross-section in FIG. 6B, the shear pin 46 has a waist 48. The waist 48 is a point along the long axis of the shear pin 46 where the diameter of the shear pin 46 is narrower than the diameter of the shear pin 46 elsewhere along the long axis of the shear pin 46. As illustrated in FIG. 6B, for example, one end of the shear pin 46 is fixed to the joining member 44 and the other end of the shear pin 46 is fixed to the distal end portion 5 of the basket legs 11a and 11c. Referring to FIG. 6C, the shear pin 46 breaks at the waist 48 upon the application of a predetermined force to the basket 10. FIG. 6C illustrates a preferred embodiment in which one half of the broken shear pin 46 remains attached to the joining member 44 and the other half of the broken shear pin 46 remains attached to the basket leg 11c. In a preferred embodiment, the shear pin 46 is rounded to avoid sharp ends that may puncture surrounding tissue.

Figure 7A:
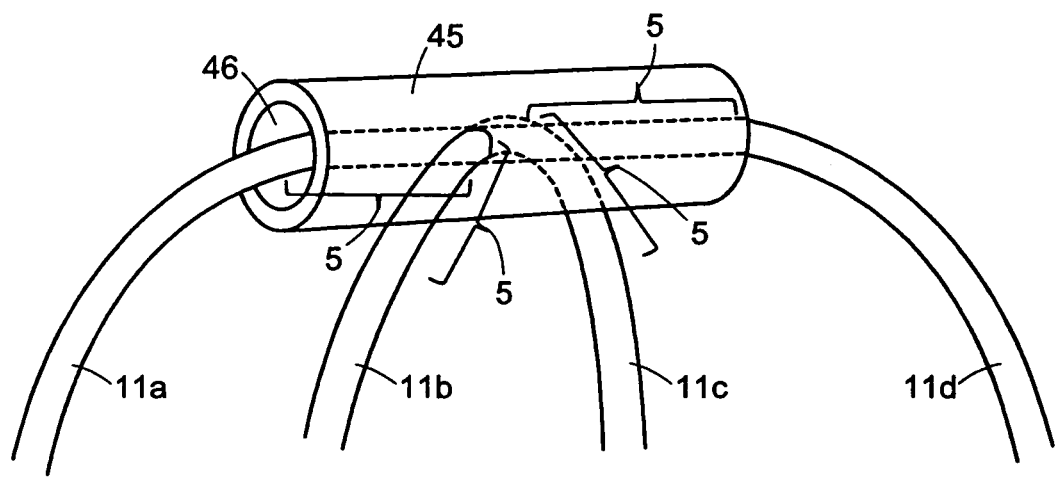
FIG. 7A illustrates an embodiment of the distal end portions of the basket legs according to the invention in which the distal tips of the legs are disposed within a tubular joining member.
Figure 7B:
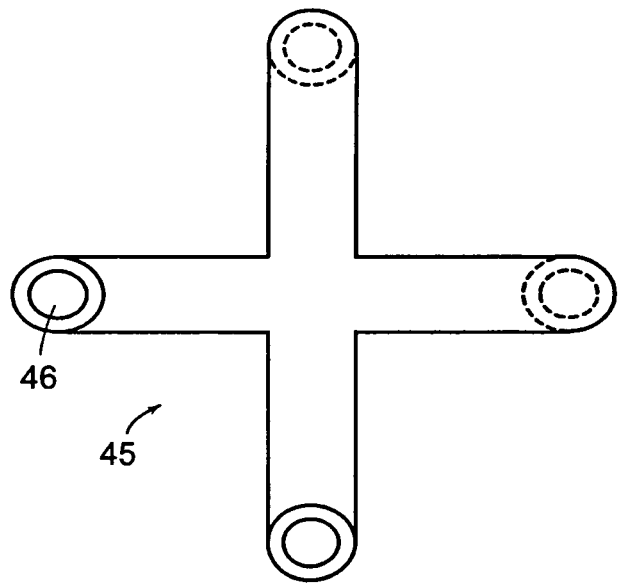
FIG. 7B illustrates a cross-shaped tubular joining member.
Figure 7C:
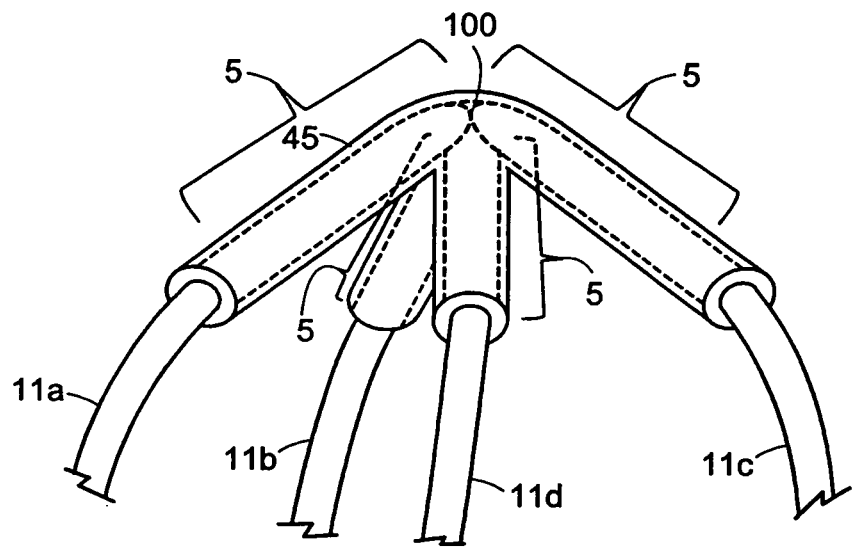
FIG. 7C illustrates an embodiment of the distal end of the basket legs according to the invention in which the distal tips of the legs are disposed within a cross-shaped joining member.
Figure 7D:
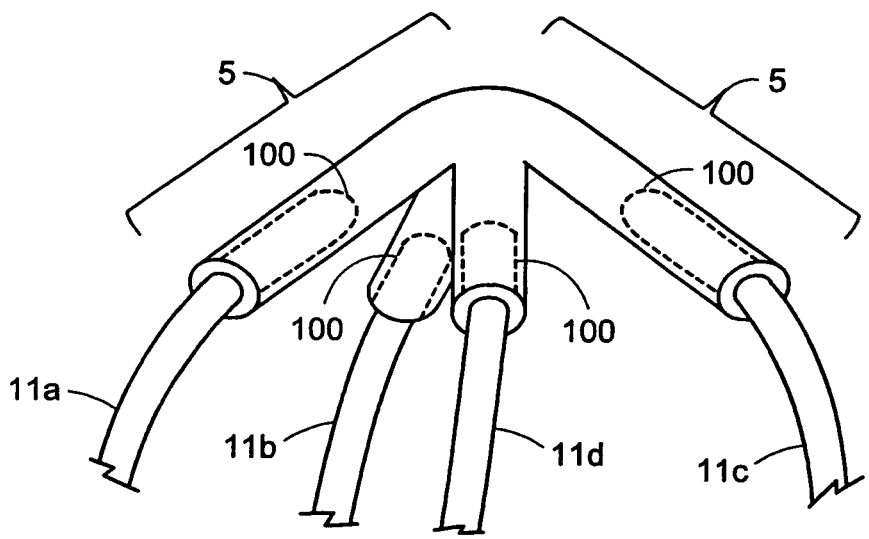
FIG. 7D illustrates an embodiment of the distal end of the basket legs according to the invention in which the distal tips of the legs are disposed within a cross-shaped joining member.

Referring to FIG. 7A, in an embodiment according to the invention, the joining member 45 is a tubular member 45 with a lumen 46, wherein the distal end portions 5 of one or more legs 11 are disposed within the lumen 46 of the tubular member 45. One or more legs 11 may also be inserted through the sides of the tubular member 45. Referring to FIG. 7B, in another embodiment, the tubular member 45 is in the shape of a cross, wherein the distal end portion 5 of the legs 11 may be disposed within the lumen 46 of the cross shaped tubular member 45. The cross shaped tubular member 45 may prevent sharp broken edges of the legs 11 from injuring the surrounding tissue of a patient once they have broken in the practice of the invention. Referring to FIG. 7C, in an embodiment according to the invention, the distal end portions 5 of one or more legs 11 are disposed within the lumen 46 of the cross-shaped tubular member 45 that is illustrated in FIG. 7B. In an embodiment, the distal end portions 5 of the one or more legs 11 may be joined to each other by soldering, welding or the like and have a break point 6 or may be joined by magnetic energy as described herein. In another embodiment, the distal end portions 5 of the legs 11 may be joined by a substance that is electrically, thermally, or chemically alterable, or may be joined by an adhesive. In an embodiment, the distal end portions 5 of one or more legs 11 are not joined to the tubular member 45 but are free floating within the lumen 46 of tubular member 45. Referring to FIG. 7D, in another embodiment, the distal end portion 5 of one or more legs 11 are joined to the tubular member by soldering, welding or the like. In another embodiment, the distal end portion 5 of the legs 11 may be joined to the tubular member 45 with one or more shear pins 46, as described herein. In an embodiment, the tubular member 45 may be loose fit on the distal ends 100 of one or more legs 11 or may fit the legs 11 tightly. In an alternative embodiment, at least a portion of the tubular member 45 is made of a substance which is frangible, or which is electrically, thermally, or chemically alterable, such that there is a break point 6 in the tubular member 45.

Figure 8A:
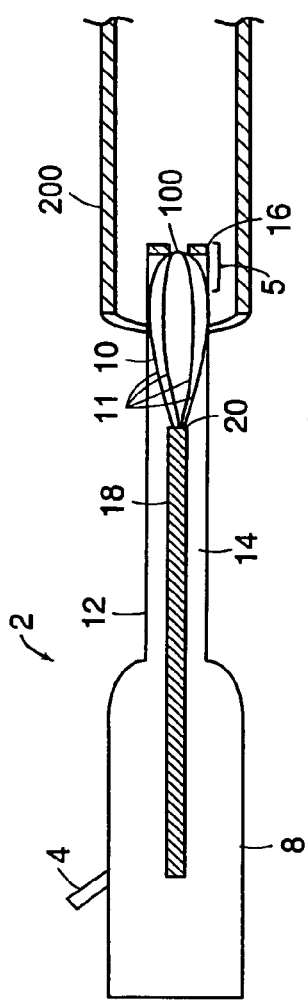
FIG. 8A illustrates one embodiment of a medical retrieval device with a basket according to the invention with the basket in a collapsed position.
Figure 8B:
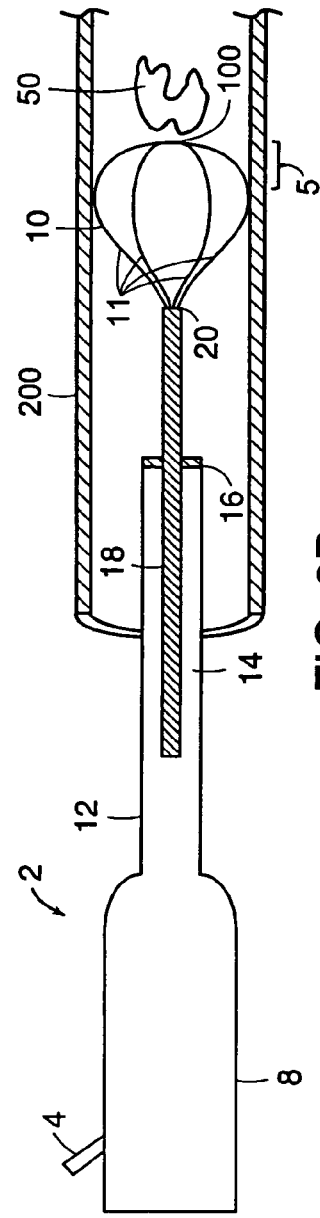
FIG. 8B illustrates one embodiment of a medical retrieval device with a basket according to the invention with the basket in an expanded position.
Figure 8C:
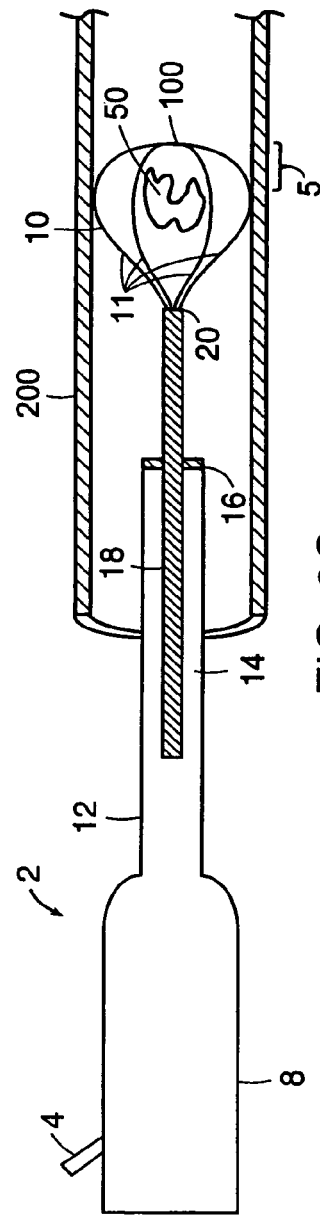
FIG. 8C illustrates one embodiment of a medical retrieval device with a basket according to the invention with the basket in an expanded position containing a material.

In yet another aspect, the invention relates to methods for retrieving material from a body using any of the devices according to the invention. Referring to FIGS. 8A-8E, material (e.g., biological or foreign) 50 can be retrieved from a body by using the basket 10, in which at least one leg 11 of the basket 10 is a frangible, as described herein. Referring to FIG. 8A, a retrieval device 2 with a basket 10 is inserted into a body tract 200 with the basket 10 in the collapsed or retracted position within the sheath 12. In an embodiment, the distal end portions 5 of the legs 11 are held together by a magnetic force. In another embodiment, the distal end portions 5 of at least two legs 11 are held together by a joining member 44 and at least one shear pin 46. In another embodiment, the distal end portion 5 of at least one leg 11 is made of, or coated with, an adhesive substance or with a substance with physical characteristics that are altered in response to an electrical, chemical, or thermal change, as described herein. Referring to FIG. 8B, in an embodiment the basket 10 is moved into the extended position by extending the basket 10 out of the distal end 16 of the sheath 12. Referring to FIG. 8C, the basket 10 is maneuvered via one or more actuators 4 on the proximal handle 8 of the retrieval device 2 until the material 50 is enclosed within the basket 10. Referring to FIG. 8D, the material 50 is captured within the basket 10 by moving the basket 10 relative to the sheath 12 to close the basket legs 11 around the material 50. With the material 50 so gripped or held by the basket 10, the basket 10 can normally be withdrawn from the body tract 200 to remove the material 50 from the body tract 200. The material 50 that can be captured with basket 10 according to the invention includes, for example, a thrombus, embolus, foreign body, calculus, or a stone, such as a kidney stone, ureteral stone, urinary bladder stone, gall bladder stone, stone within the biliary tree, tumor, or polyp.

Referring to FIG. 8E, in the event of a complication during the retrieval process that requires the release of the material 50 from the basket 10 within the body tract 200, the invention provides methods by which at least one leg 11 can be broken and/or dissociated from the other legs, for example, upon the application of a predetermined force to the basket 10 or to at least one leg 11. The predetermined force may be provided by the device 12 itself or by an external feature of the device 12. For example, a predetermined force may be applied by advancing the sheath 12 distally in the direction of the basket 10 or, alternatively, by withdrawing the basket 10 proximally, until the distal sheath end 16 and the proximal end 20 of the basket 10 meet. Force is applied from the distal sheath end 16 against the basket 10, causing the legs 11 to compress the material 50. In an embodiment, when the predetermined magnitude of the force on at least one of the legs 11 is applied, at least one of the frangible basket legs 11 fails at the break point 6. In another embodiment, when a predetermined force is applied to the basket 10 this causes at least one leg 11 to dissociate from at least one other leg 11. The material 50 is released from the basket 10 when the break point 6 is broken and/or at least one leg 11 dissociates from at least one other legs 11. Although FIG. 8E illustrates an embodiment according to the invention in which only one leg 11 breaks or dissociates from the other legs 11, more than one or all of the legs 11 may dissociate from the others.

In an embodiment, still referring to FIGS. 8A-8E, a basket 10 that has been inserted by an operator into a site in a body tract 200 is placed into its open/expanded position by reducing the magnitude of the magnetic field. The basket 10 can then be manipulated by the operator to place the material 50 within the basket 10. The magnitude of the magnetic field can then be increased to cause the basket 10 to close around the material 50 and capture it. Under normal circumstances, the basket 10 and captured material 50 are then withdrawn by the operator from the body. Alternatively, the magnitude of the magnetic field may be reduced and the basket 10 allowed to open and release the material 50 within the body tract 200. The basket 10 can then be removed from the body tract 200 without the captured material 50.

In the methods of the invention that include an electrical, thermal, or chemical change, still referring to FIGS. 8A-8E, a basket 10 that has been inserted by an operator into a site in the body is placed into its open/expanded position by advancing the sheath 12 distally in the direction of the basket 10 or, alternatively, by withdrawing the basket 10 proximally, until the distal sheath end 16 and the proximal end 20 of the basket 10 meet. The basket 10 can then be manipulated by the operator to place the material 50 within the basket 10. The sheath 12 can then be advanced proximally or, alternatively, the basket 10 can be extended distally, to close the basket 10 around the material 50 and capture it. Under normal circumstances, the basket 10 and captured material 50 are then withdrawn by the operator from the body tract 200. Alternatively, a suitable electrical charge or change, thermal change, or chemical change may be applied to the at least one leg 11, thereby altering the physical characteristics of the substance that is used to join at least two legs 11 or used to manufacture at least a portion of at least one leg 11. The at least one leg 11 breaks and/or dissociates from at least one other leg or is opened by the use of a predetermined force and the material 50 is released within the body tract 200. The basket 10 can then be removed from the body tract 200 without the captured material 50.

Variations, modifications, and other implementations of what is described herein will occur to those of ordinary skill in the art without departing from the spirit and the scope of the invention. Accordingly, the invention is to be defined not only by the preceding illustrative description.

What is claimed is:

1. A medical retrieval device, comprising:
   a sheath including a proximal end and a distal end;
   a handle at the proximal end of the sheath; and
   a basket having a collapsed position when the basket is within the sheath and an expanded position when the basket is extended past the distal end of the sheath, the basket comprising a plurality of legs comprising at least three legs, wherein each leg has a distal end with a distal tip and a proximal end, and a substantially uniform cross-sectional shape from the proximal end to the distal end, the at least three legs joined at their distal tips when in an expanded closed position, and wherein the at least three legs are configured to magnetically attract and join together at their distal tips.

2. The device of claim 1, wherein the at least three legs that are magnetically joined together are configured to dissociate upon the application of a predetermined force to the basket.

3. The device of claim 2, wherein the at least three legs are capable of magnetically rejoining after dissociating.

4. The device of claim 1, wherein the at least three legs that are magnetically joined together are configured to dissociate upon a change in magnitude of magnetic field that magnetically joins the legs.

5. The device of claim 1, wherein the distal end of at least one of the legs is formed of a magnetic material.

6. The device of claim 1, wherein the basket comprises four legs configured to magnetically attract and join together at their distal tips.

7. The device of claim 1, wherein one of the at least three legs includes a magnetic material at its distal end and the other two legs do not include the magnetic material.

8. The device of claim 1, wherein each of the at least three legs has substantially the same cross-sectional shape from the proximal end to the distal end.

9. The device of claim 1, comprising at least two closure mechanisms, wherein extending and retracting the basket within the sheath provides a first closure mechanism, and magnetic attraction and joining of the distal tips of the at least three legs of the basket provides a second closure mechanism.

10. A method for removing a material from a body tract, comprising the steps of:
    inserting a medical retrieval device into a body tract, the device comprising:
       a sheath including a proximal end and a distal end; and
       a basket extending through the sheath, the basket having a collapsed position when the basket is within the sheath and an expanded position when the basket is extended past the distal end of the sheath, the basket comprising a plurality of legs comprising at least three legs, wherein each leg has a distal end with a distal tip and a proximal end, and a substantially uniform cross-sectional shape from the proximal end to the distal end, the at least three legs configured to magnetically attract and join together at their distal tips;
    moving the basket into the expanded position;
    maneuvering the device until the material is trapped inside the basket; and
    withdrawing the device from the body tract.

11. The method of claim 10, further comprising the step of dissociating the at least three legs that are magnetically joined together.

12. The method of claim 11, further including releasing the material trapped in the basket upon dissociation of the at least three legs.

13. The method of claim 11, wherein the step of dissociating the at least three legs that are magnetically joined together includes one of applying a predetermined force to the basket to dissociate the legs or reducing a magnetic field that magnetically joins the legs.

14. The method of claim 11, wherein the step of dissociating the at least three legs that are magnetically joined together includes forcibly retracting the basket into the sheath.

15. A medical retrieval device, comprising:
    a sheath including a proximal end and a distal end;
    a handle at the proximal end of the sheath; and
    a basket having a collapsed position when the basket is within the sheath and an expanded position when the basket is extended past the distal end of the sheath, the basket being capable of a closed expanded configuration and an open expanded configuration, the basket comprising three or more legs, each leg having a proximal end and a distal end with a distal tip, wherein a first leg includes a magnetic material and is configured to magnetically attract and releasably join the distal tips of two or more second legs when in the closed expanded configuration, and wherein the two or more second legs do not include the magnetic material.

16. The medical retrieval device of claim 15, wherein each leg has a substantially uniform cross-sectional shape from the proximal end to the distal end.

\* \* \* \* \*

UNITED STATES PATENT AND TRADEMARK OFFICE
CERTIFICATE OF CORRECTION

PATENT NO. : 8,685,039 B2
APPLICATION NO. : 12/656283
DATED : April 1, 2014
INVENTOR(S) : Little et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 634 days.

Signed and Sealed this
Thirtieth Day of May, 2017

Michelle K. Lee
*Director of the United States Patent and Trademark Office*